US00PP31734P2

(12) United States Plant Patent

Kerley et al.

(10) Patent No.: US PP31,734 P2
(45) Date of Patent: May 5, 2020

(54) *PETUNIA* PLANT NAMED 'KERPICOT'

(50) Latin Name: *Petunia x atkinsiana*
Varietal Denomination: KERPICOT

(71) Applicants: Timothy Kerley, Cambridge (GB); Sarah Kerley, Cambridge (GB); David Kerley, Cambridge (GB); Priscilla Kerley, Cambridge (GB)

(72) Inventors: Timothy Kerley, Cambridge (GB); Sarah Kerley, Cambridge (GB); David Kerley, Cambridge (GB); Priscilla Kerley, Cambridge (GB)

( * ) Notice: Subject to any disclaimer, the term of this patent is extended or adjusted under 35 U.S.C. 154(b) by 0 days.

(21) Appl. No.: 16/350,670

(22) Filed: Dec. 17, 2018

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.13, 356.1, 356.16
CPC ... A01H 5/02; A01H 5/00; A01H 6/82; A01H 6/824; A01H 6/1424; A01H 6/42; A01H 6/14
See application file for complete search history.

(56) References Cited

PUBLICATIONS

USDA, Agricultural Research Service, National Plant Germplasm System. 2019, retrieved on Sep. 5, 2019, retrieved from the Internet at https://npgsweb.ars-grin.gov/gringlobal/taxonomydetail.aspx?102385, one page. (Year: 2019).*
Upov Pluto Plant Variety Database 20190905, retrieved on Sep. 5, 2019, retrieved from the Internet at https://www.upov.int/pluto/en/index.jsp, one page. (Year: 2019).*

* cited by examiner

*Primary Examiner* — June Hwu
(74) *Attorney, Agent, or Firm* — Cassandra Bright

(57) ABSTRACT

A new and distinct *Petunia* cultivar named 'KERPICOT' is disclosed, characterized by a semi-trailing, free-branching growth habit, and violet flowers with white rims. The plants are more tolerant to rain than the average *Petunia*. The new variety is a *Petunia*, normally produced as an outdoor garden or container plant.

2 Drawing Sheets

Figure 1:
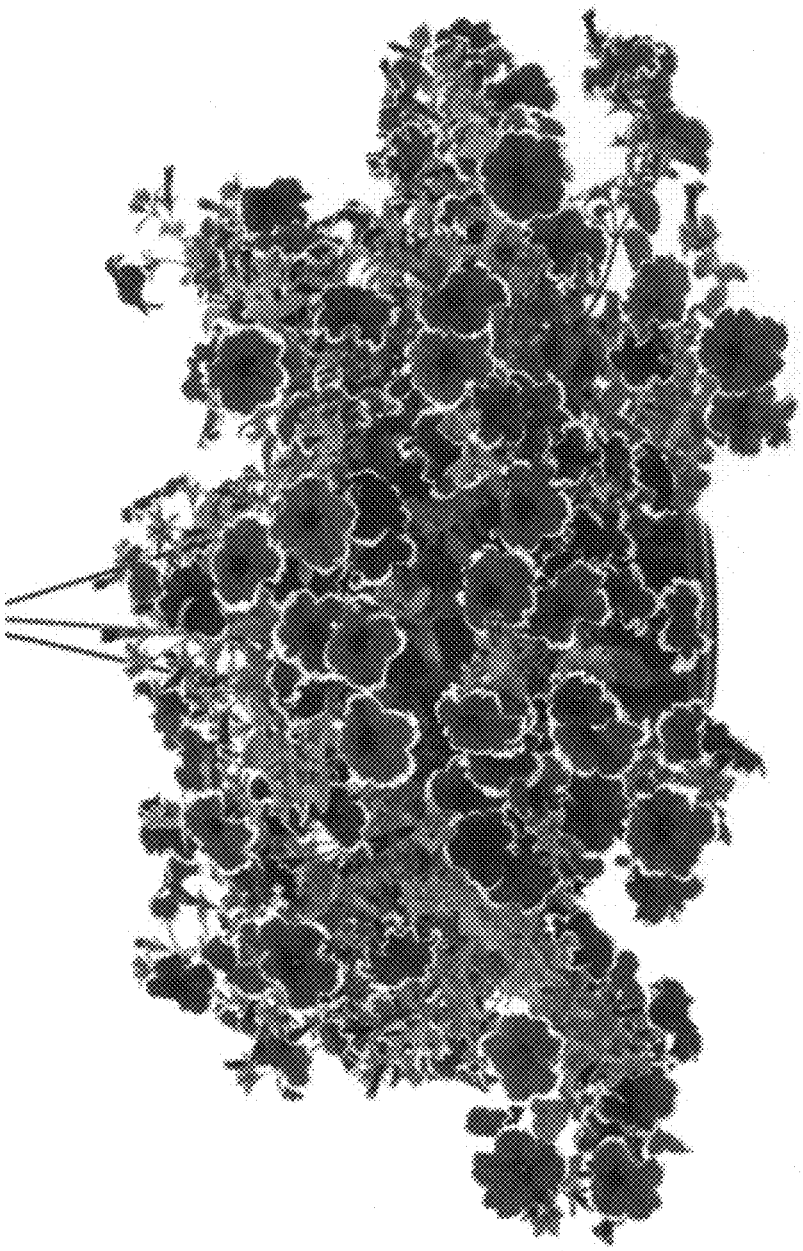

Latin name of the genus and species: *Petunia* x *atkinsiana.*
Variety denomination: 'KERPICOT'.

BACKGROUND OF THE INVENTION

'KERPICOT' is a product of a breeding and selection program for ornamental *Petunia* varieties to be vegetatively propagated. The new plant of the present invention comprises a new and distinct cultivar of *Petunia* plant.

'KERPICOT' is a seedling resulting from the crossing of the unpatented proprietary *Petunia atkinsiana* referred to as '12-691-1' with the pollen parent, an unpatented proprietary *Petunia atkinsiana* referred to as '11-397-4', conducted in August 2013. The selection of the new variety was made in May 2014, by the inventor at a research greenhouse located in Cambridge, UK. Date of first sale was Jan. 7, 2018, in the United States. This sale was made directly by the inventor or one who obtained the claimed invention directly or indirectly from the inventor. This sale and all public disclosures made before the filing of this application fall within the exception allowed under 102(b)(1).

'KERPICOT' was first asexually reproduced by vegetative terminal cuttings at a research greenhouse in Cambridge, UK, September 2014. The new cultivar has been found to retain its distinctive characteristics through successive asexual propagations.

SUMMARY OF THE INVENTION

The cultivar 'KERPICOT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERPICOT' These characteristics in combination distinguish 'KERPICOT' as a new and distinct *Petunia* cultivar:

1. Stable white rim on flowers.
2. Day-length neutral flowering. Flower bud initiation occurs in day lengths of less than 10 hours.
3. Semi trailing plant habit.
4. Free branching habit.
5. More tolerant to rain than the average *Petunia.*

PARENT COMPARISON

Plants of the new cultivar 'KERPICOT' are similar to plants of the seed parent in most horticultural characteristics, however, plants of the new cultivar 'KERPICOT' differ in the following:

1. '12-691-1' has an unstable white rim, while 'KERPICOT' has a stable white rim.
2. '12-691-1' has longer branches than 'KERPICOT'.
3. '12-691-1' does not flower across the top of the plant, as does 'KERPICOT'.
4. '12-691-1' is not as tolerant to cold as 'KERPICOT'.

Plants of the new cultivar 'KERPICOT' are similar to plants of the pollen parent in most horticultural characteristics however, plants of the new cultivar 'KERPICOT' differ in the following:

1. '11-397-4' has longer branches than 'KERPICOT'.
2. '11-397-4' has paler foliage than 'KERPICOT'.
3. '11-397-4' is more trailing than 'KERPICOT'.

COMMERCIAL COMPARISON

Plants of the new cultivar 'KERPICOT' can be compared to the commercial variety *Petunia* 'Surfinia Blue Picotee', unpatented. These varieties are similar in most horticultural characteristics; however, 'KERPICOT' differs in the following:

1. 'Surfinia Blue Picotee' has smaller flowers than 'KERPICOT'.
2. 'Surfinia Blue Picotee' has shorter, narrower sepals than 'KERPICOT'.
3. 'Surfinia Blue Picotee' has more star-shaped flowers than 'KERPICOT'.
4. 'Sanguna Blue Picotee' has an unstable rim pattern, while 'KERPICOT' has a stable rim pattern.
5. Basal leaves of 'Surfinia Blue Picotee' turn yellow, while leaves of 'KERPICOT' do not.

Plants of the new cultivar 'KERPICOT' can also be compared to the commercial variety *Petunia* 'PEHY0014' U.S. Plant Pat. No. 27,856. These varieties are similar in most horticultural characteristics; however, 'KERPICOT' differs in the following:

1. 'PEHY0014' has red-purple flowers, while 'KERPICOT' has violet flowers.
2. 'PEHY0014' has an upright plant habit, while 'KERPICOT' has a semi-trailing habit.
3. 'PEHY0014' has a larger white flower rim than 'KERPICOT'.
4. 'PEHY0014' has an unstable rim pattern, while 'KERPICOT' has a stable rim pattern.
5. Flower margin of 'PEHY0014' is not undulating, while flower margin of 'KERPICOT' is undulating.

BRIEF DESCRIPTION OF THE PHOTOGRAPHS

The accompanying photograph in FIG. 1 illustrates in full color a typical plant of 'KERPICOT' grown in a greenhouse, in Cambridge, United Kingdom.

Figure 2:
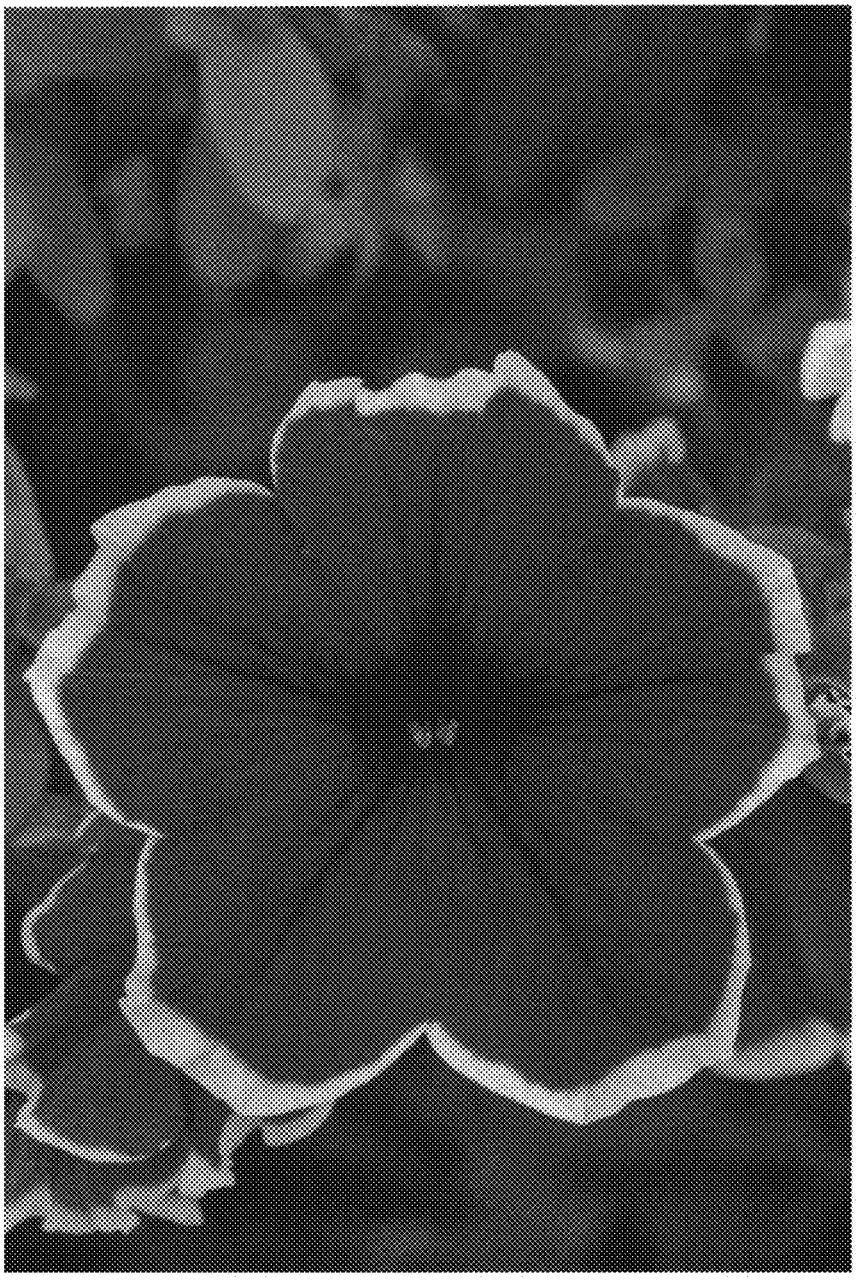

FIG. 2 illustrates in full color a typical mature flower of 'KERPICOT' during Spring. Age of the plant photographed is approximately 60 days from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KERPICOT' plants grown in greenhouse in Cambridge, United Kingdom, under natural lighting. Measurements were taken during April of 2018. The plants were approximately 10 weeks from a rooted cutting in a 30 cm hanging basket. The growing temperature ranged from 20° C. to 35° C. during the days, 17° C. to 23° C. during the nights. Measurements and numerical values represent averages of typical plant types.

Botanical classification: *Petunia* x *atkinsiana* 'KERPICOT'.

PROPAGATION

Time to initiate roots: Approximately 10 days at 20° C.
Root description: Fibrous, freely branching.

PLANT

Growth habit: Spreading, mounded.
Pot size of plant described: 30 cm hanging basket.
Height: 17.3 cm to top of flowering plane.
Plant spread: 37.3 cm.
Growth rate: Medium.
Length of primary lateral branches: 29.8 cm.
Diameter of lateral branches: 0.4 cm.
Quantity of primary lateral branches: 6.
Characteristics of primary lateral branches:
- *Color*.—Young stem: RHS Yellow-Green 144A.
- *Mature stem*.—RHS Yellow-Green 146B.
- *Texture*.—Densely pubescent.
- *Strength*.—Medium.

Internode length: 2.83 cm.

FOLIAGE

Leaf:
- *Arrangement*.—Alternate before flowering, then opposite.
- *Form*.—Simple.
- *Quantity*.—11 per branch.
- *Average length*.—5.3 cm.
- *Average width*.—4.1 cm.
- *Shape of blade*.—Elliptic.
- *Apex*.—Acute on young leaves, becoming obtuse.
- *Base*.—Obtuse.
- *Margin*.—Entire.
- *Texture of top surface*.—Sparsely pubescent.
- *Texture of bottom surface*.—Sparsely pubescent.
- *Color*.—Young foliage upper side: Darker than RHS Yellow-Green 144A. Young foliage under side: RHS Yellow-Green 146B. Mature foliage upper side: RHS Green NN137B. Mature foliage under side: RHS Yellow-Green 147B.
- *Venation*.—Type: Pinnate. Venation color upper side: Between RHS Yellow-Green 146C and D. Venation color under side: RHS Yellow-Green 146B.
- *Petiole*.—Length: 0.3 cm. Diameter: 0. 2 cm. Color: RHS Yellow-Green 146C. Texture: Densely pubescent.

FLOWER

Natural flowering season: Spring and Summer in Cambridge, United Kingdom.
Days to flowering from rooted cutting: 21 to 28 days.
Inflorescence and flower type and habit: Simple, salverform.
Rate of flower opening: 2 to 3 days from bud to fully opened flower.
Flower longevity on plant: 5 to 6 days.
Approximate quantity of flowers per plant: 26.
Persistent or self-cleaning: Self-cleaning.
Bud:
- *Shape*.—Oblong.
- *Length*.—2.6 cm.
- *Diameter at apex*.—0.9 cm.

*Diameter at base.*—0.4 cm.
*Texture.*—Densely pubescent.
*Color.*—RHS Violet N92A; apex White N155A.

Flower size:
*Diameter.*—7 cm.
*Length.*—About 2.5 cm.
*Flower tube diameter at distal end.*—About 0.8 cm.
*Flower tube diameter at proximal end.*—About 0.3 cm.

Petals:
*Length from tube.*—3 cm.
*Length of free portion.*—1.6 cm.
*Width.*—3.4 cm.
*Quantity.*—5.
*Shape.*—Obovate.
*Appearance.*—Velvety.
*Texture, upper surface.*—Glabrous.
*Texture, lower surface.*—Sparsely pubescent.
*Apex.*—Obtuse.
*Margin.*—Entire, undulating.
*Lobing.*—Strong.

Color:
*When opening.*—
*Upper surface.*—Darker than RHS Purple N81A. Rim White NN155D. White rim about 4 to 7 mm thick.
*Lower surface.*—Near RHS Purple 83C. Rim White NN155D. White rim about 4 to 7 mm thick. Veins Violet 86B.
*Fully opened.*—
*Upper surface.*—Darker, richer than RHS Violet N87A, with darker venation (Violet 86A). Rim whiter than White NN155D. White rim about 4 to 7 mm thick.
*Lower surface.*—Near RHS Violet 87A, darker towards base. Rim whiter than White NN155D. White rim about 4 to 7 mm thick. Veins Violet 86B.
*Flower throat (inside).*—RHS Violet-Blue N92B.
*Flower throat, vein.*—RHS Violet-Blue N92C.
*Flower tube (outside).*—RHS Violet 83C.
*Flower tube, vein.*—RHS Yellow-Green N144C.

Corolla tube:
*Length.*—2.93 cm.
*Diameter at distal end.*—1.77 cm.
*Diameter at proximal end.*—2 cm.
*Texture, inner surface.*—Glabrous.
*Texture, outer surface.*—Densely pubescent.

Sepals:
*Quantity per flower.*—5 fused along lower half.
*Shape.*—Cuneate.
*Length.*—1.8 cm.
*Width.*—0.73 cm.
*Margin.*—Entire.
*Apex.*—Obtuse.
*Texture, upper and lower surfaces.*—Densely pubescent.
*Color.*—Upper Surface: Between RHS Yellow-Green 147B. Lower Surface: RHS Yellow-Green 147B.

Peduncle:
*Strength.*—Strong.
*Aspect.*—45 degrees to stem.
*Length.*—3 cm.
*Diameter.*—3 mm.
*Texture.*—Densely pubescent.
*Color.*—Near RHS Yellow-Green 146B.

Fragrance: None.

REPRODUCTIVE ORGANS

Stamens:
*Number.*—5 partially fused to inside of corolla tube.
*Length.*—2 cm.
*Filament length.*—8.7 mm.
*Filament color.*—RHS Purple N77B.

Anthers:
*Length.*—2 mm.
*Shape.*—Reniform.
*Color.*—Near RHS Green-Grey 188B.
*Pollen.*—Color: Near RHS Blue 115C.

Pistil:
*Number.*—1.
*Length.*—1.47 cm.
*Style.*—Length: 8.7 mm. Color: RHS Yellow-Green 144C.
*Stigma.*—Shape: Linear. Color: RHS Yellow-Green 144C. Ovary Color: RHS Yellow-Green 144A.

OTHER CHARACTERISTICS

Seeds and fruits: Not observed to date.

Disease/pest resistance: Neither resistance nor susceptibility to the normal diseases and pests of *Petunia* have been observed. Typical well-known diseases include: *Botrytis cineria, Fusarium, Pythium, Phytophthora*, and *Rhizoctonia* species. Typical well-known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'KERPICOT' as herein illustrated and described.

* * * * *